US009700201B2

(12) United States Patent
Bex et al.

(10) Patent No.: US 9,700,201 B2
(45) Date of Patent: Jul. 11, 2017

(54) RAPID MEASUREMENT OF VISUAL SENSITIVITY

(71) Applicants: The Schepens Eye Research Institute, Inc., Boston, MA (US); The Ohio State University, Columbus, OH (US)

(72) Inventors: Peter Bex, Concord, MA (US); Michael Dorr, Cambridge, MA (US); Luis Lesmes, Watertown, MA (US); Zhong-Lin Lu, Columbus, OH (US)

(73) Assignees: The Schepens Eye Research Institute, Inc., Boston, MA (US); The Ohio State University, Columbus, OH (US)

( * ) Notice: Subject to any disclaimer, the term of this patent is extended or adjusted under 35 U.S.C. 154(b) by 140 days.

(21) Appl. No.: 14/399,136

(22) PCT Filed: May 9, 2013

(86) PCT No.: PCT/US2013/040434
§ 371 (c)(1),
(2) Date: Nov. 5, 2014

(87) PCT Pub. No.: WO2013/170091
PCT Pub. Date: Nov. 14, 2013

(65) Prior Publication Data
US 2015/0150444 A1 Jun. 4, 2015

Related U.S. Application Data

(60) Provisional application No. 61/644,889, filed on May 9, 2012.

(51) Int. Cl.
*A61B 3/02* (2006.01)
*A61B 3/06* (2006.01)
(Continued)

(52) U.S. Cl.
CPC ............ *A61B 3/022* (2013.01); *A61B 3/0025* (2013.01); *A61B 3/06* (2013.01); *A61B 3/032* (2013.01)

(58) Field of Classification Search
CPC ........... A61B 3/06; A61B 3/063; A61B 3/066; A61B 3/022; A61B 3/032
(Continued)

(56) References Cited

U.S. PATENT DOCUMENTS

2008/0137037 A1* 6/2008 Kratzer .................... A61B 3/06
351/243
2009/0244113 A1 10/2009 Bergquist et al.
(Continued)

FOREIGN PATENT DOCUMENTS

WO WO-2011135364 A2 11/2011

OTHER PUBLICATIONS

Kelly. Motion and vision. I. Stabilized images of stationary gratings. J Opt Soc Am. Sep. 1979;69(9):1266-74.
(Continued)

*Primary Examiner* — Huy K Mai
(74) *Attorney, Agent, or Firm* — Mintz Levin Cohn Ferris Glovsky and Popeo, P.C.

(57) ABSTRACT

Data is received characterizing a result of a first visual sensitivity test assessing capacity to detect spatial form across one or more different target sizes, and different contrasts. Using the received data, one or more first parameters defining a first estimated visual sensitivity for a first range of contrasts and a second range of spatial frequencies is determined. One or more second parameters defining a second estimated visual sensitivity for a third range of contrasts and a fourth range of spatial frequencies is determined using the one or more first parameters and a statistical inference by at least presenting a first visual stimulus, receiving a response, and determining a second visual stimulus based at least on the response and at least a rule. The one or more second parameters is provided. Related apparatus, systems, techniques and articles are also described.

23 Claims, 15 Drawing Sheets

(51) Int. Cl.
*A61B 3/00* (2006.01)
*A61B 3/032* (2006.01)
(58) Field of Classification Search
USPC .................................................. 351/242, 239
See application file for complete search history.

(56) References Cited

U.S. PATENT DOCUMENTS

2010/0007851 A1* 1/2010 Lu ......................... A61B 3/028
351/242
2011/0063571 A1 3/2011 Duffy

OTHER PUBLICATIONS

Kelly. Motion and vision. II. Stabilized spatio-temporal threshold surface. J Opt Soc Am. Oct. 1979;69(10):1340-9.

Campbell et al., Application of Fourier analysis to the visibility of gratings. J Physiol. Aug. 1968;197(3):551-66.

De Valois et al., Psychophysical studies of monkey vision. 3. Spatial luminance contrast sensitivity tests of macaque and human observers. Vision Res. Jan. 1974;14(1):75-81.

Hou et al., qCSF in clinical application: efficient characterization and classification of contrast; sensitivity functions in amblyopia. Invest Ophthalmol Vis Sci. Oct. 2010;51(10):5365-77.

Kontsevich et al., Bayesian adaptive estimation of psychometric slope and threshold. Vision Res. Aug. 1999;39(16):2729-37.

Kujala et al., Bayesian adaptive estimation: the next dimension. J Math Psychol. 2006;50(4)369-89.

Lesmes et al., Bayesian adaptive estimation of the contrast sensitivity function: the quick CSF method. J Vis. Mar. 30, 2010;10(3):17.1-21.

McAnany et al., Contrast sensitivity for letter optotypes vs. gratings under conditions biased toward parvocellular and magnocellular pathways. Vision Res. May 2006;46(10):1574-84.

Rovamo et al., Cortical magnification factor predicts the photopic contrast sensitivity of peripheral vision. Nature. Jan. 5, 1978;271(5640):54-6.

Watson, A. Estimation of local spatial scale. J Opt Soc Am A. Aug. 1987;4(8):1579-82.

\* cited by examiner

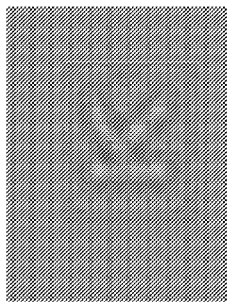
FIG. 2C
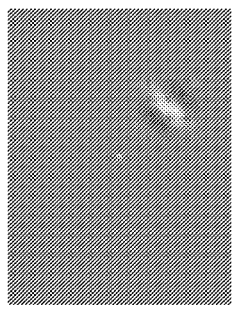
FIG. 2A
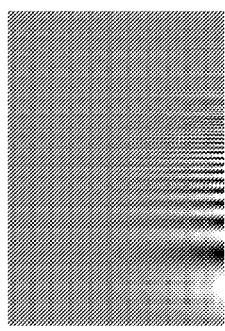
FIG. 2E
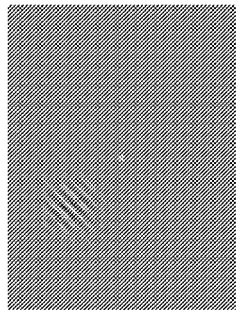
FIG. 2D
FIG. 2B
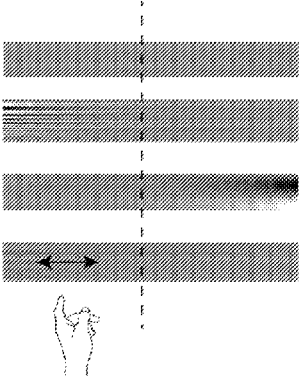
FIG. 2F
FIG. 2G

RAPID MEASUREMENT OF VISUAL SENSITIVITY

RELATED APPLICATIONS

This application is a national stage application, filed under 35 U.S.C. §371, of International Application No. PCT/US2013/040434, filed on May 9, 2013, which claims priority under 35 U.S.C. §119(e) to U.S. Provisional Application No. 61/644,889 filed May 9, 2012, the contents of each of which are hereby incorporated by reference in their entirety.

TECHNICAL FIELD

The subject matter described herein relates to visual contrast sensitivity assessment.

BACKGROUND

Adaptive testing methods that apply computationally intense algorithms have been used to estimate spatial, temporal, and spatio-temporal contrast sensitivity functions (CSFs) in vision. These quick CSF methods apply Bayesian adaptive inference to estimate the parameters of contrast sensitivity functions. These methods are primarily focused on isolating frequency-specific channels in the visual system using narrow-band grating stimuli.

SUMMARY

In one aspect, data is received characterizing a result of a first visual sensitivity test assessing capacity to detect spatial form across one or more different target sizes, and different contrasts. Using the received data, one or more first parameters defining a first estimated visual sensitivity for a first range of contrasts and a second range of spatial frequencies is determined. One or more second parameters defining a second estimated visual sensitivity for a third range of contrasts and a fourth range of spatial frequencies is determined using the one or more first parameters and a statistical inference by at least presenting a first visual stimulus, receiving a response, and determining a second visual stimulus based at least on the response and at least a rule. The one or more second parameters is provided.

In another aspect, data is received characterizing a result of a first subjective visual sensitivity pre-test assessing capacity to detect spatial form across different contrasts. Using the received data, one or more first parameters defining a first estimated visual contrast sensitivity function is determined. One or more second parameters defining a second estimated visual contrast function is determined using the one or more first parameters as a priori inputs to an iterative Bayesian inference, the iterative Bayesian inference being performed by at least presenting a first visual stimulus, receiving a response, determining a second visual stimulus based at least on the response and at least Bayes rule, and iterating until a stopping condition is satisfied. The one or more second parameters is provided.

One or more features can be included. For example, the first visual sensitivity test can include at least one of: drawing a line on a spatial frequency image that indicates a transition between a visible contrast and an invisible contrast, the line characterizing a visual sensitivity; or indicating at least one of a presence or an absence of targets of differing spatial frequency. The first visual stimulus and second visual stimulus can include one or more of: a band-pass frequency stimulus, a band-pass frequency letters, and a localized windowed grating. Each of the first visual stimulus and second visual stimulus can include a flickering and a band-pass filtered letter. One or more of a temporal frequency of the flickering and a spatial frequency of the band-pass filtered letter can vary between the first visual stimulus and the second visual stimulus.

Each of the first visual stimulus and the second visual stimulus can include dynamic band-pass letter charts. The one or more first parameters can include one or more of a peak sensitivity, a peak spatial frequency, a low frequency truncation level, and a bandwidth. The first visual sensitivity test can be performed using a mobile device. The determining the one or more second parameters can further include providing instructions to view the first visual stimulus at a viewing distance, the vising distance determined by using a camera associated with the mobile device to measure a viewing distance. The determination of the one or more second parameters can be based on the viewing distance. A visual function can be assessed by at least using the one or more second parameters to compare visual sensitivity based on at least one or more of the following: at different visual field locations, in different illumination conditions, in photopic and mesopic conditions, and at two or more levels of external illumination noise.

The first visual stimulus can be selected based on at least previously determined parameters. The first visual stimulus can be a band-pass frequency stimulus and the previously determined parameters can characterize a probability. The first visual stimulus can be presented using a display. A response can be received relating to the first visual stimulus. The probability based on at least a Bayes rule and a received response can be updated. Iterating can occur until a stopping criterion is satisfied.

The providing can include one or more of a transmitting, a displaying, a storing, and a computing of the one or more second parameters. The determining the one or more second parameters can include iteratively presenting visual stimulus, receiving a response, and determining second visual stimulus for presenting using the response and at least the rule, the rule based on at least a Bayes rule. The one or more first parameters can be used as a priori values for a Bayesian inference.

Articles of manufacture are also described that comprise computer executable instructions permanently stored (e.g., non-transitorily stored, etc.) on computer readable media, which, when executed by a computer, cause the computer to perform operations herein. Similarly, computer systems are also described that may include a processor and a memory coupled to the processor. The memory may temporarily or permanently store one or more programs that cause the processor to perform one or more of the operations described herein. In addition, methods can be implemented by one or more data processors either within a single computing system or distributed among two or more computing systems.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 2A-G are example spatial frequency images;

DETAILED DESCRIPTION

Figure 1:
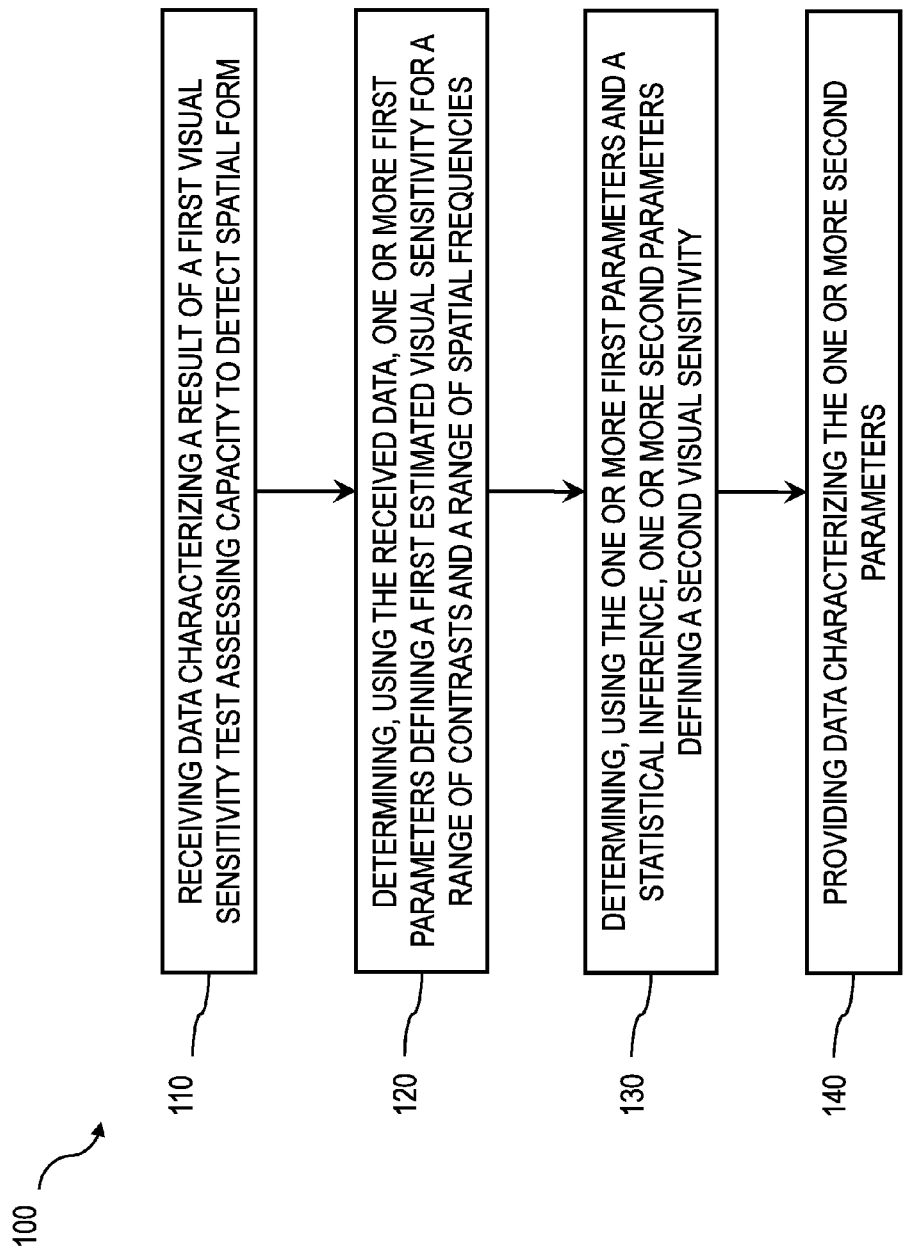
FIG. 1 is a process flow diagram illustrating a method of rapidly measuring visual sensitivity.

FIG. 1 is a process flow diagram 100 illustrating a method of rapidly measuring visual sensitivity. Data is received at 110 characterizing a result of a first visual sensitivity test. The visual sensitivity test assesses a capacity of a subject or user to detect spatial form across different target sizes, contrasts, and spatial orientations.

The first visual sensitivity test, or contrast sensitivity pre-task, can include a test that requires a user to draw or indicate a line on a spatial frequency image, such as one shown in FIG. 2A. The line can indicate where the user perceives a transition between visible and invisible contrast. FIG. 2B illustrates the spatial frequency image shown in FIG. 2A with a sample line drawn. The line characterizes the user's visual sensitivity for at least a range of contrasts and/or a range of spatial frequencies. However, this characterization is subjective due to the subjectivity of decision criterion between what is visible and invisible. These subjective tasks can be confounded by either response or motor biases that do not strictly depend on sensory factors. For example, motor precision is highest at the beginning of the trace (low frequencies), and the ballistic hand movement of the tracing behavior can result in imprecision at the end of the trace (high frequencies). Additionally, local adaptation of spatial frequency can change the subjective percept of the contrast sensitivity function as eyes move across the test pattern. Subjective measures of visual function can provide rapid, roughly accurate, but imprecise starting points for more precise, objective measurements.

The first visual sensitivity test can include a test that comprise ribbons of a contrast sensitivity image (e.g., as shown in FIG. 2G), which the subject attempts to align (e.g., using a swiping of the ribbons on a touch sensitive device). The subject attempts to align the visible and invisible regions of the different ribbons into a straight line. Adjustment based on the perception and judgment of linear patterns can be more precise than judgment of curvilinear patterns.

The first visual sensitivity test can include a test that requires the subject or user to indicate a presence or absence of targets of differing spatial frequencies; for example, FIG. 2C and FIG. 2D show images with localized sine-wave gratings of differing frequencies and can be incorporated into a visual sensitivity test. FIG. 2C illustrates a sine-wave grating with a lower frequency than the sine-wave grating shown in FIG. 2D. A subject or user can indicate whether the sine-wave grating is present. A grating stimulus is characterized as a two-dimensional sinusoid and can be used in vision research because gratings are the basis functions for two-dimensional Fourier analysis. The grating can further include a letter, such as is illustrated in FIG. 2E and FIG. 2F. Objective (forced-choice) tasks are designed to be bias-free, but have longer testing times than subjective tasks.

Figure 3:
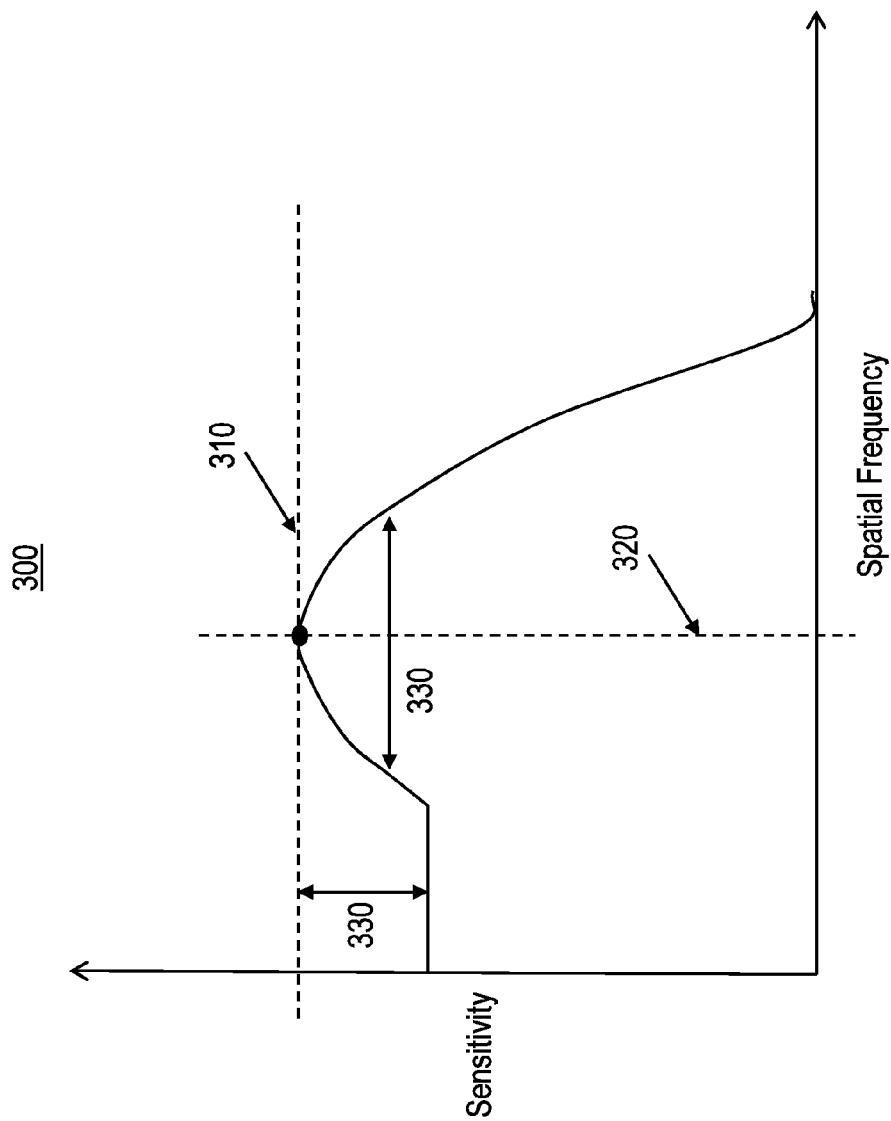
FIG. 3 demonstrates a typical person's contrast sensitivity across spatial frequency and illustrates a parameterized model of contrast sensitivity.

Referring again to FIG. 1, one or more first parameters are determined at 120. The first parameters define a first estimated visual sensitivity for a range of contrasts and a range of spatial frequencies. FIG. 3 demonstrates a typical shape of a user's contrast sensitivity as a function of spatial frequency and illustrates a parameterized model of contrast sensitivity for a range of contrasts and a range of spatial frequencies (also referred to as a CSF). Spatial frequency is shown on the horizontal axis and contrast sensitivity on the vertical axis. The model illustrated in FIG. 3 includes a parameter for peak sensitivity 310, peak spatial frequency 320, band-width 330 measured at half power, and a low frequency truncation level 330 being a difference between the peak sensitivity 310 and a plateau region at lower spatial frequency.

Referring again to FIG. 1, one or more second parameters defining a second visual sensitivity are determined at 130 using the one or more first parameters and a statistical inference. The one or more second parameters are determined by at least presenting a first visual stimulus, receiving a response, and determining a second visual stimulus using the response and at least a rule. The presenting a first visual stimulus, receiving a response, and determining a second visual stimulus using the response and at least a rule can be performed iteratively to determine the one or more second parameters. The one or more second parameters can be provided at 140. Providing the one or more second parameters can include one or more of transmitting to another device, displaying at a monitor or screen, storing in memory, and/or performing calculations.

A statistical inference is a process of drawing conclusions from data that is subject to random variation, for example, observational errors or sampling variation. Frequentist inference and Bayesian inference are example classes of statistical inference. Bayesian inference is a method of inference in which Bayes' rule is used to update the probability estimate for a hypothesis as additional evidence is learned.

In an example, when Bayesian inference is used, the one or more second parameters are determined by updating the one or more first parameters, which serve as a priori probabilities. The updated parameters can be iteratively updated using new information until a stopping criterion (e.g., a number or updates, or a confidence in the precision of the parameters) is reached.

In this manner, a subjective contrast sensitivity judgment can be used to seed the Bayesian prior for a subsequent objective test. A first visual test result or prior that is easy to collect, and represents the specific individual about to be tested, can provide a valuable starting point to accelerate the assessment by the objective task. For example, having a subject trace out the transition between visible and invisible on an image (e.g., FIG. 2A and FIG. 2B) provides preliminary estimates of contrast sensitivity, including information about the peak sensitivity and peak frequency.

The first visual stimulus and the second visual stimulus can be determined to help improve an estimate of the visual sensitivity of a user. The first visual stimulus and second visual stimulus can include one or more of band-pass frequency stimulus, band-pass frequency letters, and localized windowed grating. The first visual stimulus and second visual stimulus can include a flickering band-pass filtered letter. The temporal frequency of the flickering and the spatial frequency of the band-pass filtered letter can vary between the first visual stimulus and the second visual stimulus. Band-pass filtered letters can be selected from any number of letters. Pre-literate children can benefit from a four-letter version (e.g., Landolt C or Tumbling E), while traditional ten letter Sloan subset or twenty six letters for the entire alphabet can be used. Using more letters lowers guessing rate, and can improve the convergence rate of probability estimates.

Figure 4:
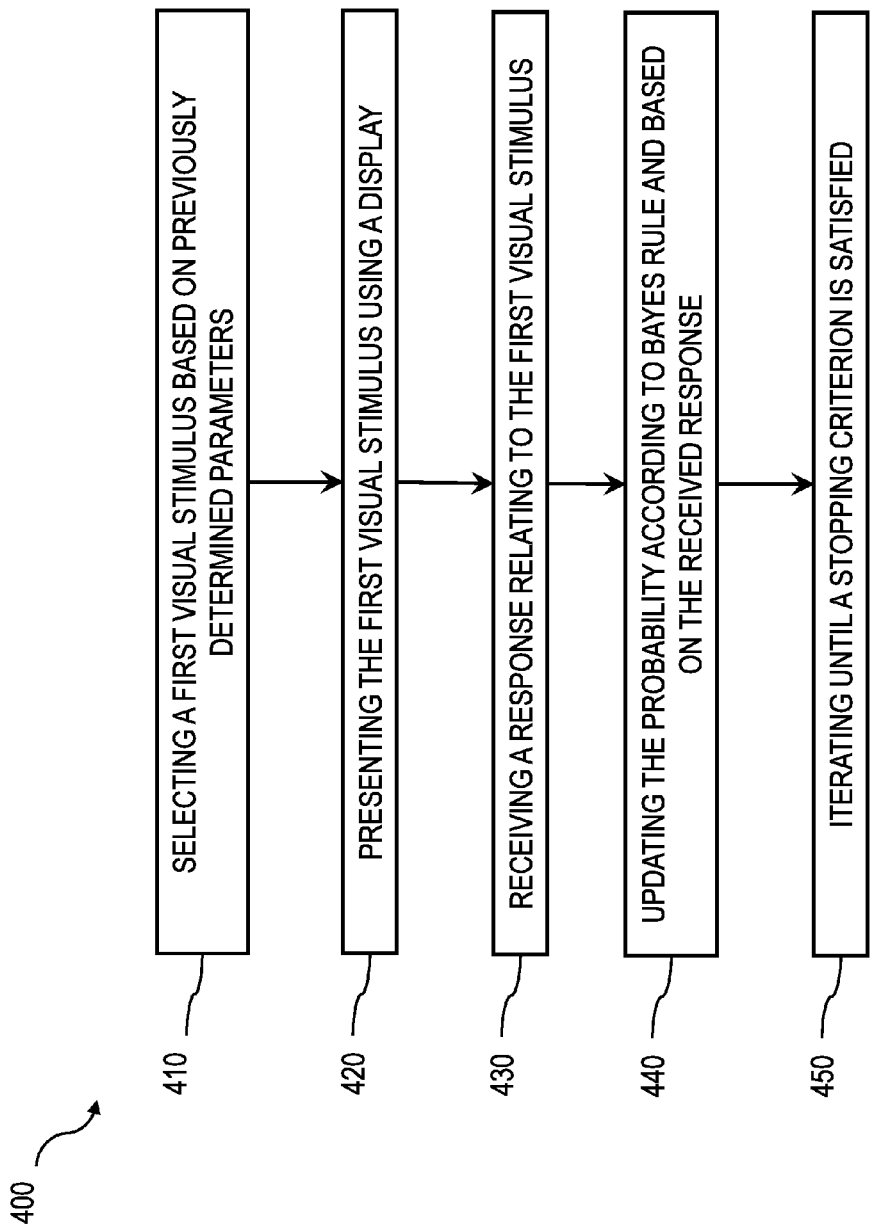
FIG. 4 is a process flow diagram illustrating a method of determining the one or more second parameters.

FIG. 4 is a process flow diagram 400 illustrating a method of determining the one or more second parameters. A first visual stimulus is selected at 410. The selection is based on previously determined parameters (e.g., the first parameters). The first visual stimulus is a band-pass frequency stimulus and the previously determined parameters characterize a probability. The first visual stimulus can be presented at 420. The presenting can be to a user or subject. A response relating to the first visual stimulus is received at 430. The probability can update according to Bayes rule and based on the received response at 440. The process can iterate until a stopping criterion is satisfied at 450.

Figures 5A, 5B:
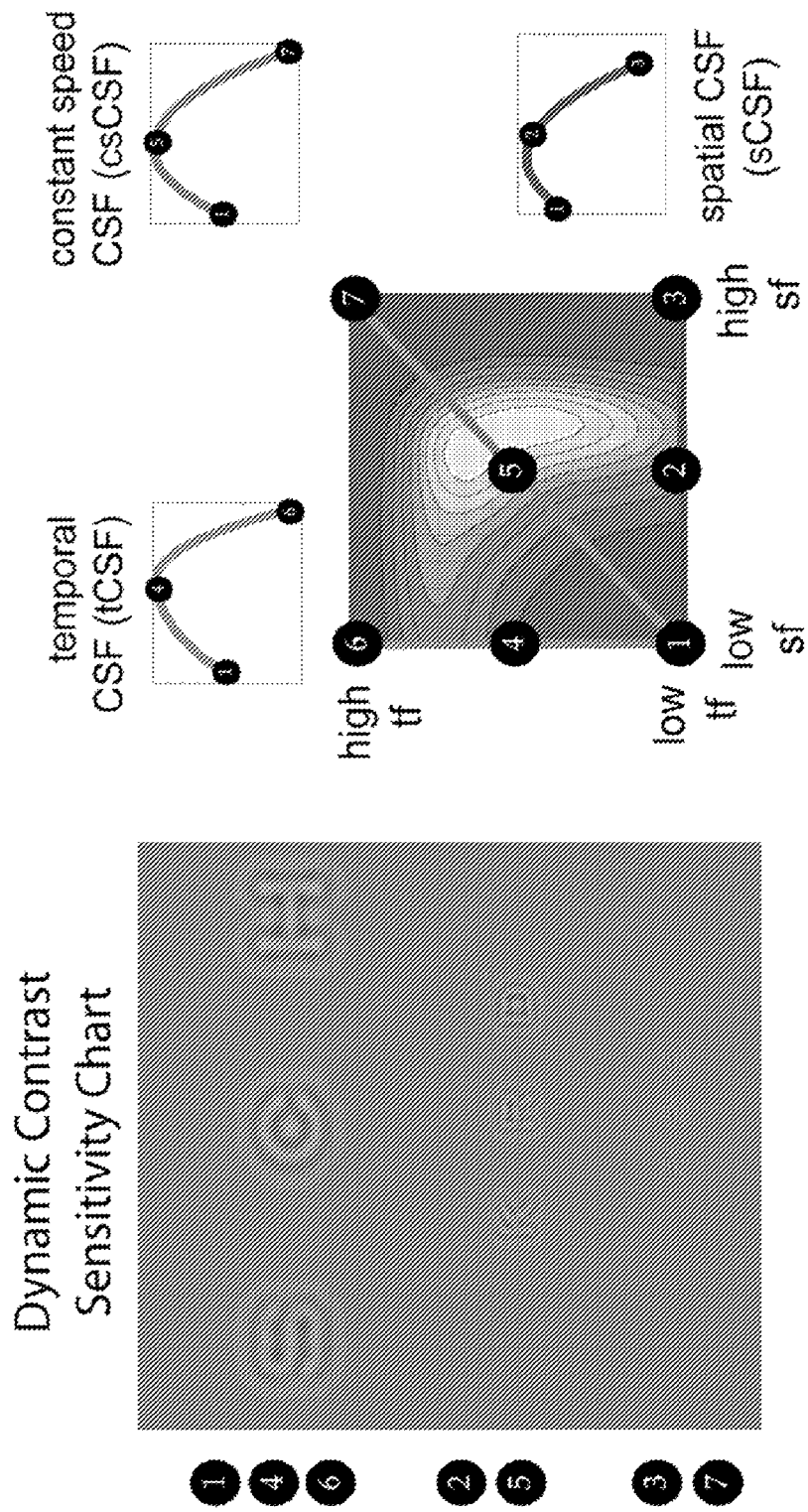
FIG. 5A is a diagram illustrating a dynamic band-pass letter chart that can be used as a visual stimulus.
FIG. 5B is a diagram illustrating an example of a spatio-temporal contrast sensitivity surface.

FIG. 5A is a diagram illustrating a dynamic band-pass letter chart that can be used as a visual stimulus. Traditional letter charts are printed on paper media; therefore, the test stimuli are static and pre-determined. The dynamic contrast sensitivity chart illustrated includes three rows of band-pass filtered letters at varying spatial frequencies and temporal frequencies. The dynamic band-pass letter chart can also be flickered at constant or varying rates. FIG. 5B is a diagram illustrating an example of a spatio-temporal contrast sensitivity surface. Temporal frequency is shown in the vertical axis and spatial frequency is shown in the horizontal axis. The spatio-temporal contrast sensitivity surface can also be dynamic and flicker at constant or varying rates. A dynamic contrast sensitivity chart can provide a better assessment of functional vision that can be more important for predicting reading and mobility. A dynamic contrast sensitivity chart can provide a better assessment of functional vision. An adaptive algorithm can adjust the size (e.g. spatial frequency), flicker (e.g. temporal frequency), and contrast of the letters to gain information about a user's contrast sensitivity.

Figure 6:
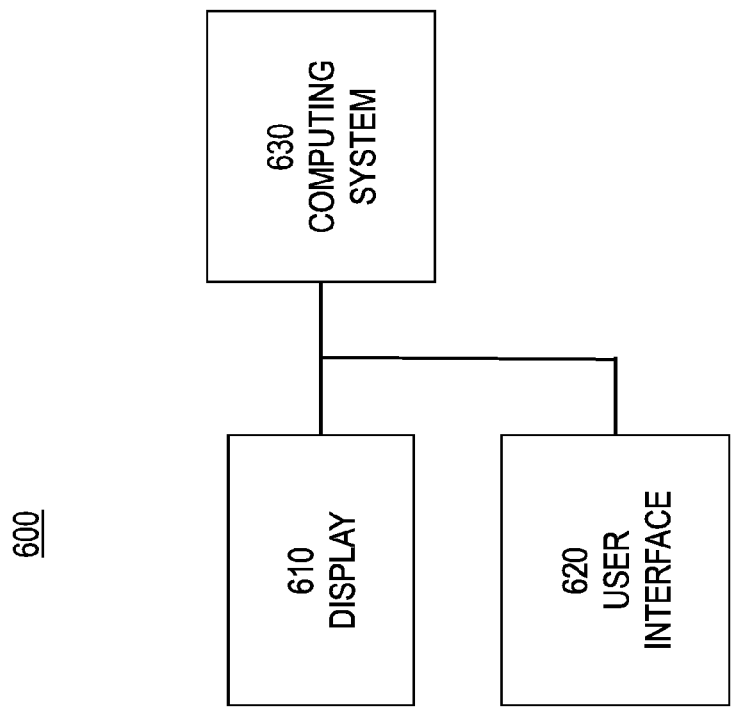
FIG. 6 is a system diagram illustrating components of a system for rapid measurement of visual sensitivity.
Figure 6:
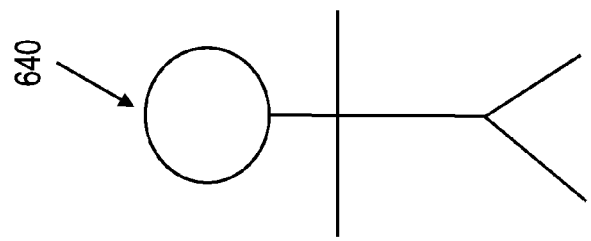

FIG. 6 is a system diagram 600 illustrating components of a system for rapid measurement of visual sensitivity. The system 600 includes a display 610 coupled to a user interface 620 and a computing system 630. A user or subject 640 can interact with the user interface 620 and/or display 610. The system can include, for example, a personal computer or a mobile device such as a smart phone or tablet computer and can have network connectivity for communication with other computing systems. The user interface 620 can integrate with the display 610, for example, as a touch screen display. Band-pass frequencies (i.e., wider range of frequencies, and more intermediate frequencies) can be accommodated based on display resolution and size. The user 620 can perform the first visual sensitivity test using the system by, for example, viewing a spatial frequency image (such as one shown in FIG. 2A) on the display 610. The user 640 can indicate or draw a line on the image using the user interface 620 where the user 640 perceives a transition between visible and invisible contrast. The computing system 630 can determine the one or more first parameters from the result of the first visual sensitivity test and determine the one or more second parameters using the statistical inference. The first visual stimulus and second visual stimulus (e.g., a dynamic band-pass letter chart like the one illustrated in FIG. 5A, or another visual stimulus) can present to the user 640 on the display 610. Identification can be done by key press of recognized letters, and/or the subject can verbally respond for recognition by a test proctor or verbal recognition software.

Since visual tests often require a specific viewing distance between a subject and the stimulus, a mobile device can provide instructions to the user for performing the first visual test and/or for viewing the visual stimulus at a viewing distance required for a particular test. For example, a mobile device can measure the viewing distance of a user before and during a test using a forward facing camera of the mobile device to estimate the viewing distance from an inter-pupillary distance. (The mean inter-pupillary distance for adults is 6.4 cm with a standard deviation of 4 mm.) Viewing distance can be measured directly or by holding the mobile device at a specified distance and calculating the visual angle subtended on the camera sensor by the pupils. Alternatively, simulating a stereo camera system by means of one camera and an accelerometer integrated in the mobile device. The subject can move the device back and forth laterally while the camera continuously records video images. The accelerometer data can be used to calculate the disparity or difference in absolute camera positions between subsequent video frames, from which a three-dimensional scene can be reconstructed that includes viewing distance. Alternatively, the user or subject waving the mobile device in front of their face for several seconds can measure viewing distance. Changes in distance throughout the experiment can be determined via measuring the size of an outline of the head and with blob matching algorithms. Alternatively, markers that are easily detectable by computer vision algorithms, such as high-contrast bull's-eye markers, can be worn by the subject, e.g., as a sticker on the forehead or on the outside of an eye patch that is used for monocular testing. Because of the known size of the marker, viewing distance can be estimated based on the size of the marker image projected onto the camera sensor.

Whereas some portable testing may use the camera merely for compliance (e.g., to interrupt testing if viewing distance changes), the camera can be used to estimate viewing distance and recalculate the visual sensitivity results based on the veridical spatial scale of the stimulus, and not the assumed spatial scale. In this implementation, data is not thrown away based on test non-compliance. Additionally, uncertainty (variability) of the spatial scale of the stimulus over the experiment (based on variability of the estimated viewing distance) can be incorporated to estimate uncertainty of the contrast sensitivity function: i.e., error estimates in the horizontal dimension of the contrast sensitivity function.

Contrast sensitivity testing applications can be implemented on mobile devices. Mobile devices are useful for testing in (1) informal home settings, in which people can test themselves regularly as part of a clinical trial, (2) medically underserved settings, in which expensive testing equipment is unavailable, and (3) inconvenient and isolated work settings (e.g., isolated working environments; theater of war), in which availability of clinical testing equipment is at a premium. Patients can be provided with a mobile device based test to take home, e.g. to monitor the progression of visual neuropathologies. This can allow frequent self-testing in the home to monitor the potential remediation following treatment or rehabilitation therapy. The device itself could be the mode of rehabilitation therapy for training methods that are currently computer based. The integrated connectivity of the device (e.g. Wi-Fi, 3G) can provide the remote health care provider with recent test results.

During laboratory-based tests, an individual running the experiment can provide instructions directly and can monitor study compliance (e.g. maintaining the correct viewing distance). During a mobile device based test, a human instructor can be available through internet (video-telephony), and the tablet's front-facing camera and computer vision algorithms can estimate the observer's distance automatically.

Figure 7:
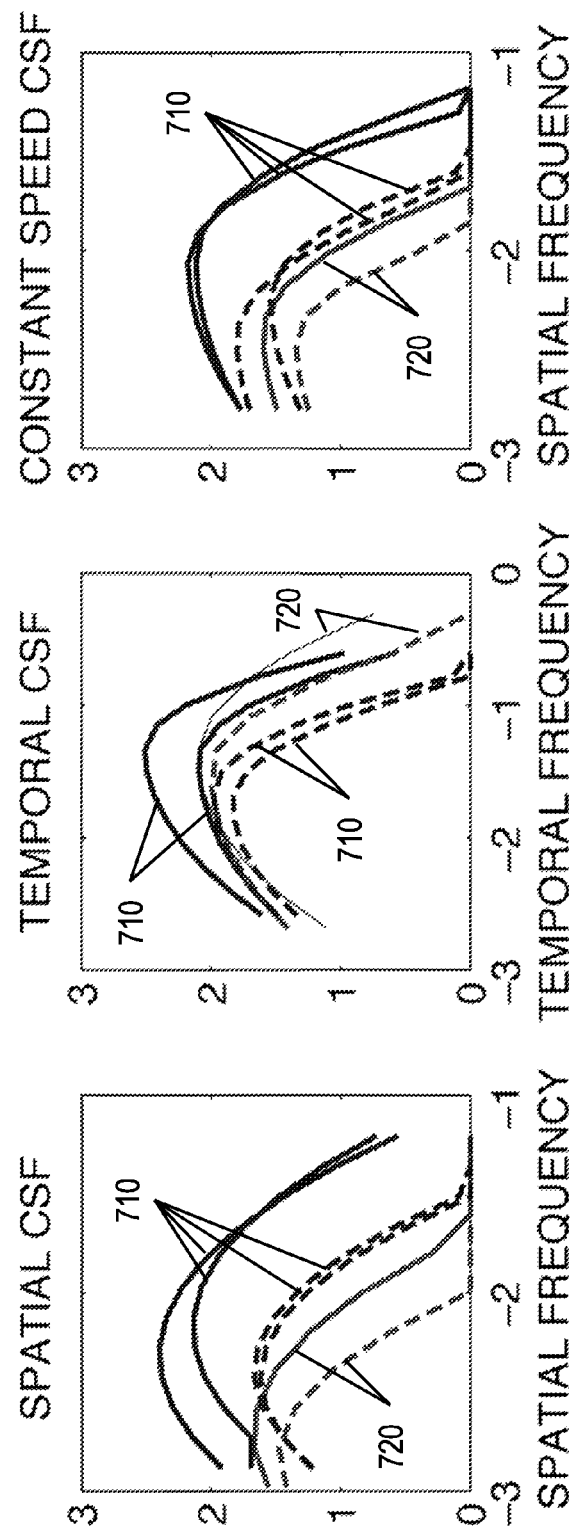
FIG. 7 is a series of plots illustrating results of measuring visual sensitivity dynamics under illumination changes.

Rapid and accurate visual sensitivity measurements can be used to assess visual sensitivity in a number of settings that were previously difficult to measure. For example, contrast sensitivity can be measured at different visual field locations, in different illumination conditions, in photopic and mesopic conditions, and at two or more levels of external illumination noise. FIG. 7 illustrates the results of measuring visual sensitivity dynamics under illumination changes. Rapidly measuring sensitivity can provide multiple measurements in different visual conditions. Each panel of FIG. 7 presents CSFs obtained from two individuals with normal vision (710) and one with impaired vision (720; Stargardt's disease) under photopic illumination (solid) and the transition to mesopic illumination (dashed) within minutes.

Figure 8:
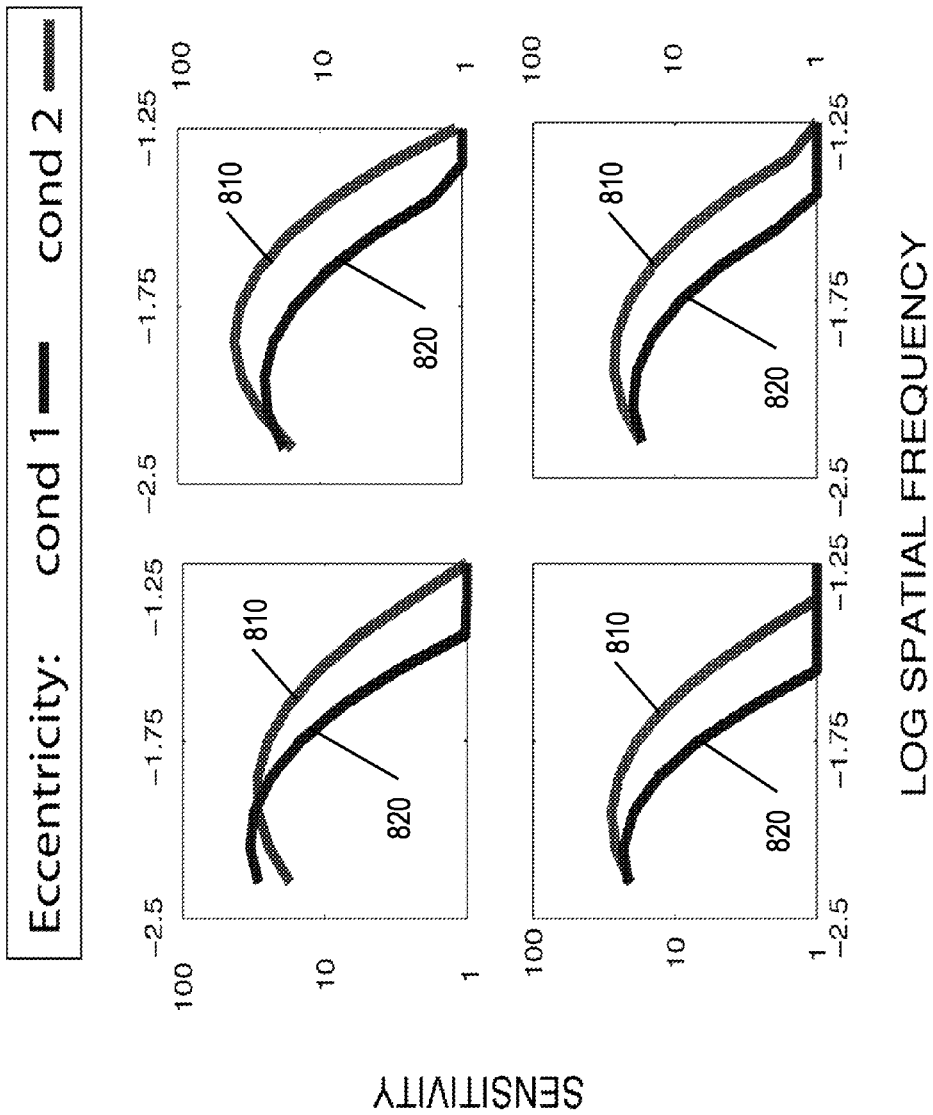
FIG. 8 is a series of plots illustrating spatial contrast sensitivities measured for one observer, for low and high retinal eccentricities along the four cardinal directions of the visual field.

FIG. 8 presents the spatial contrast sensitivities measured for one observer, for low (810) and high (820) retinal eccentricities along the four cardinal directions of the visual field. Contrast sensitivity functions were measured at different eccentricities along the horizontal and vertical meridians of the visual field. A horizontal shifting between functions measured at different eccentricities provides an approximation to the data. This can provide for the measurement of multiple contrast sensitivities across a range of spatial frequencies.

The current subject matter, may, in some implementations, provide precise contrast sensitivity assessment that is flexible enough to measure normal and impaired vision over broad ranges of illumination, eccentricity, temporal frequencies, and/or external noise conditions.

The following provides an illustrative example. The CSF characterizes functional vision, but its measurement can be time-consuming. The quick CSF method is a psychophysical method that combines Bayesian adaptive inference and a trial-to-trial information gain strategy to estimate contrast sensitivity across a range of spatial and/or temporal frequencies (i.e., the full shape of the CSF). The current subject matter, may, in some implementations, relate to improving the clinical utility of the quick CSF method, applying it to assess spatial contrast sensitivity in a low vision population, and/or comparing its results to standard clinical vision measures.

For 21 patients referred to low vision rehabilitation, spatial contrast sensitivity function is measured, from frequencies of 0.22 to 13.5 cycles per degree, in addition to Pelli-Robson contrast sensitivity, and log MAR acuity. The quick CSF algorithm is used to select the stimulus frequency and contrast presented on each trial. The full CSF is estimated from 15 quick CSF trials, from which two summary metrics can be calculated: (1) the AULCSF, which provides a global contrast sensitivity measure, and (2) CSF acuity, a high frequency metric that defines the spatial frequency at which sensitivity=2 (threshold=50%). It can be demonstrated that with as few as 15 trials, each of which last overall 1-2 minutes, the quick CSF provides a reasonably detailed assessment of visual function in people with low vision.

The AULCSF estimates obtained with the quick CSF method are correlated with Pelli-Robson sensitivity ($r=0.67$), CSF acuity is correlated with log MAR acuity ($r=-0.69$), but Pelli-Robson sensitivity and log MAR acuity are not correlated ($r=-0.14$). AULCSF estimates obtained with 15 trials are the same as those obtained with 30 trials (mean difference=2%; s.d.=18%).

The first visual sensitivity test included presenting patients with a contrast sensitivity image (Campbell, F. W., & Robson, J. G. (1968)). Application of Fourier analysis to the visibility of gratings (*J Physiol Lond*, 197, 551-66)) and having the patients trace out the entire CSF. As an alternative, the patients can trace out the peak CSF. A result of the subjective assessment can be determined from characteristics of the trace. Prior densities for the CSF parameters, $p(\theta)$, can be established based on the results of the subjective first visual sensitivity test. Prior densities, $p(\theta)$, can be defined over a grid of CSF parameters. The peaks of the marginal modes correspond to the rough estimates provided by the subjective task.

Monte Carlo inverse sampling can be used to determine N samples from the prior, $p(\theta)$. Expected information gain can be determined by calculating the information gain over Monte Carlo Samples. (Kujala J, Lukka T. Bayesian adaptive estimation: The next dimension. J Math Psychol 2006. 50(4):369-389. http://dx.doi.org/10.1016/j.jmp.2005.12.005). Potential information gained over parameter space $\Theta$ can be approximated by the following equation:

$$H_t(R_s) - H_t(R_s \mid \theta) = h\left(\int p(\theta) \psi_\theta d\theta\right) - \int h(p(\theta)) \psi_\theta d\theta \approx h\left(\frac{1}{N}\sum_f \psi_{\theta'_j}(s)\right) - \frac{1}{N}\sum_f h(\psi_{\theta'_j}(s))$$

$h(p) = -p\log(p) - (1-p)\log(1-p)$ defines the entropy of a distribution of complementary probabilities: p and 1−p. Calculating $\Psi_\theta(x)$ over the Monte Carlo samples for each possible stimulus can be possible. Given a single sampled vector of CSF parameters, $\theta'_j$, that each defines a single CSF, $S_{\theta'_j}$, the probability of a correct response (assuming a lapse rate ϵ and guessing rate γ) for a grating of frequency, f, and contrast, c, is given by a psychometric function:

$$\psi_\theta(f,c) = \gamma + (1-\gamma-\epsilon/2)\hat{\psi}(f,c)$$

in which $\hat{\Psi}(f,c)$ can originate from a family of common psychometric functions that include the log-Weibull, the logistic, or the cumulative Gaussian function.

Bayes Rule can be used to iteratively update p(θ), given a response to a stimulus. Explicit gridded priors can be used for the Bayesian update that follow each trial's outcome. To calculate the probability of the observed response (either correct or incorrect, Kontsevich L L, Tyler C W. Bayesian adaptive estimation of psychotmetric xlope and threshold. Vision Res 1999. 39(16):2729-2737. PMID: 10492833), to the stimulus s, $p(r_{correct}, s) = \psi_\theta(s)$, or $(r_{incorrect}, s) = 1 - \psi_\theta(s)$, the prior, $p_t(\theta)$, can be used to weigh the response rates defined by CSF vectors, θ, across the parameter space, $T_\theta$:

$$p(r_t \mid s_t) = \sum_\theta p(r_t, s_t) p_t(\theta)$$

This normalization factor, sometimes called "the probability of the data," is then used to update the prior $p_t(\theta)$ to the posterior $p_{t+1}(\theta)$ via Bayes Rule:

$$p_{t+1}(\theta) = \frac{P_t(\theta) p(r_t \mid \theta, s_t)}{p(r_t \mid s_t)}$$

After the observer finishes trial t, the updated posterior can be used as the prior for trial t+1. For a stopping criterion, a fixed trial number can be used. Other stopping criteria, e.g., based on the variability of the AULCSF estimate, are possible.

An implementation of a contrast sensitivity task can be a four-alternative spatial localization task. A grating can be presented at one of four locations and the subject can attempt to localize the grating. The quick CSF algorithm selects the stimulus parameters (i.e., the grating's contrast and frequency).

Figure 9:
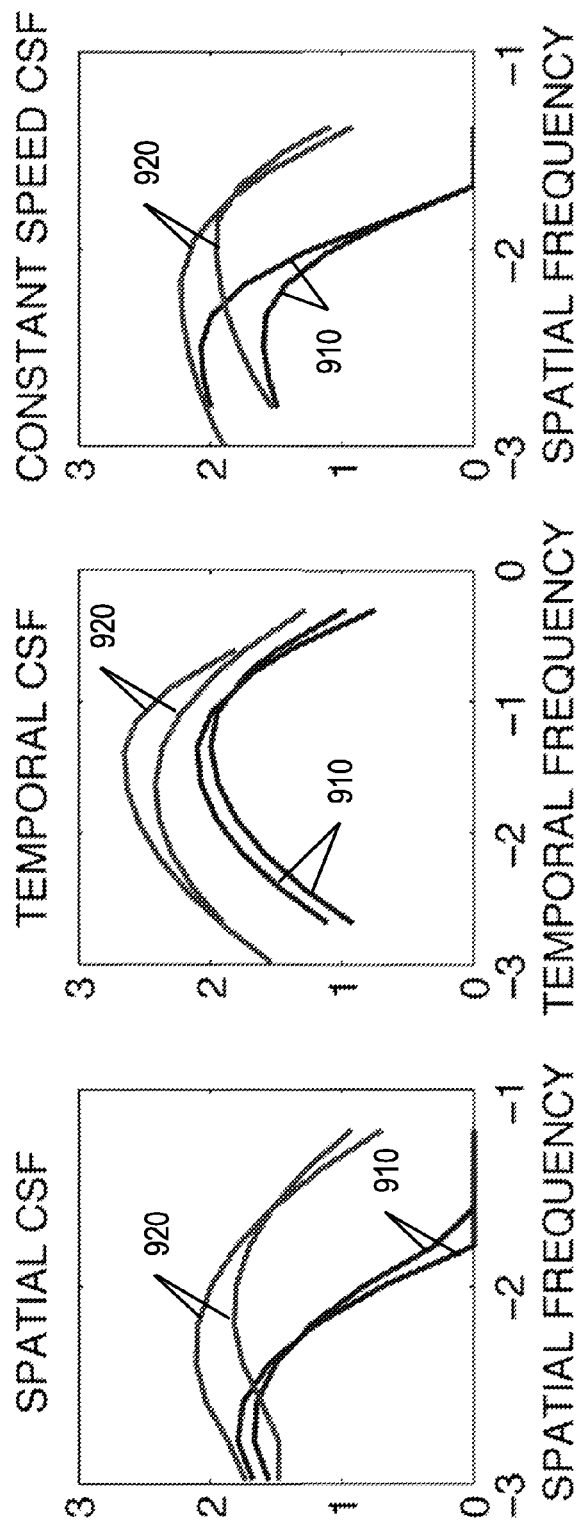
FIG. 9 is a series of plots illustrating spatial, temporal, and spatio-temporal CSF estimates obtained with 15 trials each from 4 subjects: 2 with normal vision and 2 with impaired vision.

FIG. 9 presents the spatial, temporal, and spatio-temporal CSF estimates obtained with 15 trials each from 4 subjects: 2 with normal vision (920) and 2 with impaired vision (910) (i.e. ocular albinism and Stargardt's disease). Spatial CSF were measured by band-pass filtering letter optotypes (in frequencies of cycles per object), presenting the filtered optotypes at different sizes, and having subjects identify the letters.

The ability to rapidly measure a single contrast sensitivity function makes it possible to measure several contrast sensitivity functions within a short amount of time. A more complete assessment of functional vision can involve measuring CSFs across different testing conditions: e.g., measuring CSFs at different spatial and temporal frequencies, in different eyes, at different visual field locations, in different illumination conditions (photopic vs mesopic), along different dimensions of cone color contrast space (red-green vs blue-yellow), different levels of external glare, and different levels of external noise. FIG. 7 presents spatial, temporal, and spatiotemporal sensitivity functions obtained in photopic (solid line) and mesopic (dashed line) illumination, for two observers with normal (710) vision and one with impaired vision (720; Stargardt's disease). Using 15 trials of data collection per function (<2 minutes), classical patterns of contrast sensitivity as a function of illumination are obtained. For each subject, both the peak gain and peak frequency of contrast sensitivity functions are reduced when mesopic sensitivity is compared to photopic sensitivity; the shifts to lower peak gains and lower peak frequencies are apparent in FIG. 7 and FIG. 8. FIG. 8 presents the spatial contrast sensitivities measured for one observer, for low (810) and high (820) retinal eccentricities along the four cardinal directions of the visual field.

Measurement of contrast sensitivity under different external noise conditions can aid in assessing amblyopia, especially at high spatial frequencies. Measurement of contrast sensitivity under different external glare conditions can aid in assessing cataract. Measurement of contrast sensitivity during different luminance adaptation levels can aid in assessing the impairment caused by age-related macular degeneration.

Bayesian inference can be used to estimate the contrast sensitivity function and yield a measure of confidence that is implicitly defined in the full multi-dimensional probability distribution defined over CSF parameters. Taking samples from this posterior distribution, and calculating the AULCSF generated by the corresponding set of CSF parameters, generates a distribution of AULCSF estimates. This provides a useful estimate of the variability of AULCSF estimates obtainable from a single run; this approach differs from other measures that need test and retest to estimate variability.

Spatial scale of processing at a visual field location can be assessed by measuring CSFs with fixed-cycle grating stimuli. Measuring CSFs at different eccentricities can yield functions that exhibit the same shape and peak sensitivity, but are shifted relative to each other on the log-frequency axis. The relative shift between CSFs yield an estimate of spatial scale differences between the visual field locations and can be used to characterize contrast sensitivity across the visual field. The visual field CSF method can assess contrast sensitivity independently at different visual field locations.

Stimulus selection can be applied to find the multiple stimuli that most improve contrast sensitivity assessment by presentation of the set of stimuli to the subject. This strategy represents an attempt to find synergy between different stimuli. For example, finding the best stimulus to present twice (or more) is not the same as finding the best stimulus and just presenting it twice.

The local adjustment of stimulus intensity provided by adaptive staircases (e.g., 1-up/1-down, or 3-up/1-down) can produce a sequential dependence in many psychophysical data. The simulated annealing principles that help the stimulus selection algorithm applied by the quick CSF, which avoid local minima in its optimization, also produce greater independence between successive trials, and therefore makes it difficult for observers to reliably predict what the next stimulus will be.

Figures 10A, 10B:
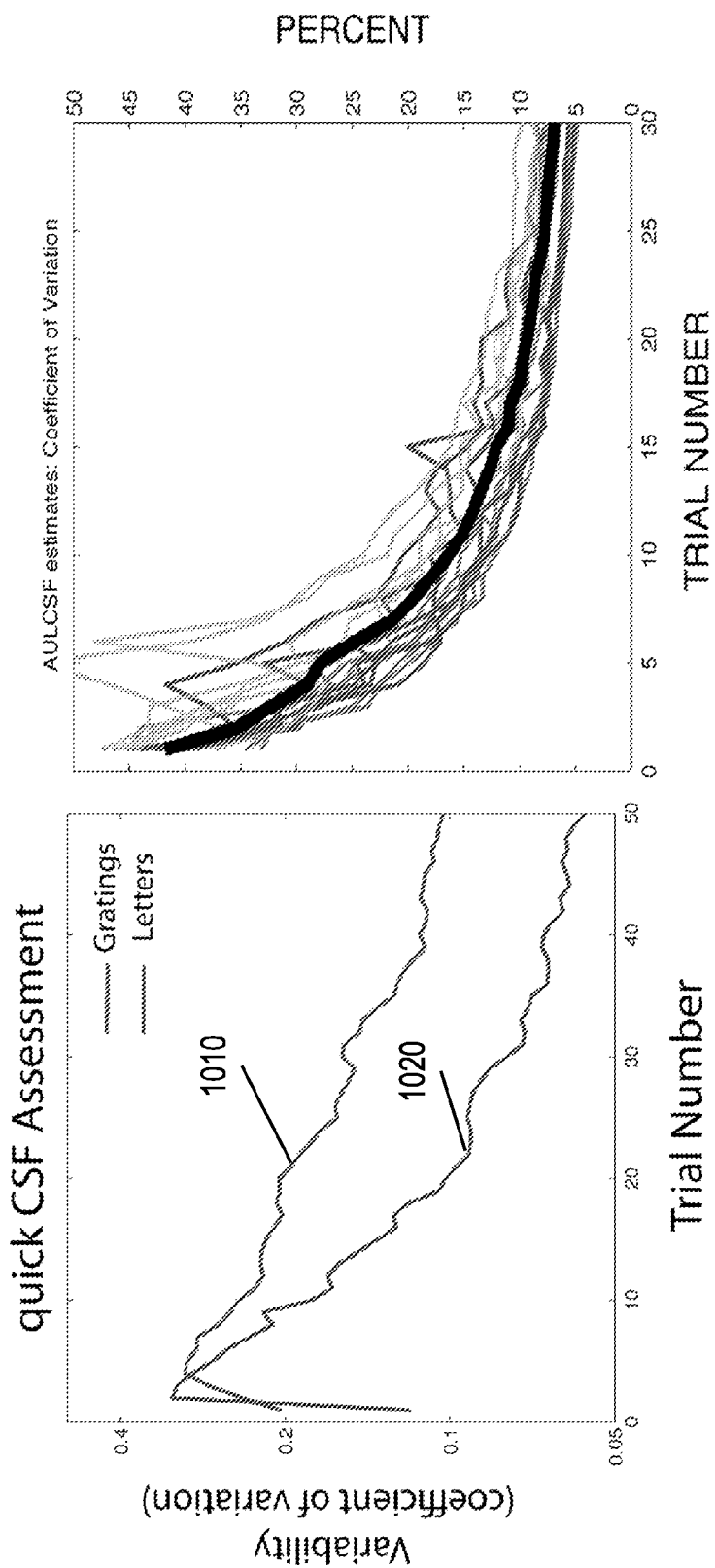
FIG. 10A is a plot illustrating a variability of area under log contrast sensitivity function (AULCSF) estimates across trial number.
FIG. 10B is a plot illustrating a coefficient of variation for AULCSF estimates.

FIG. 10A is a plot showing the variability of AULCSF estimates as a function of trial number. The convergence of AULCSF estimates is the same for broad ranges of sensitivity measured under conditions of normal and impaired vision. The rate of method convergence, defined by variability (coefficient of variation) of AULCSF estimates as a function of trial number is presented for the quick CSF method applied with grating (1010) and letter (1020) stimuli. FIG. 10B is a plot illustrating the coefficient of variation for AULCSF estimates. The Bayesian prior probability density can define the uncertainty about CSF parameters. Sampling the prior, and calculating the AULCSF for the given samples of CSF parameters, can generate a distribution of AULCSF estimates. The mean and standard deviation of this distribution provides mean and variability estimates of the AULCSF metric obtained from a single run. For both normal and impaired vision, which span a wide range of contrast sensitivity values, the convergence rates for AULCSF estimates are roughly the same. The coefficient of variation decreases to 10% after 15 trials.

Figure 11:
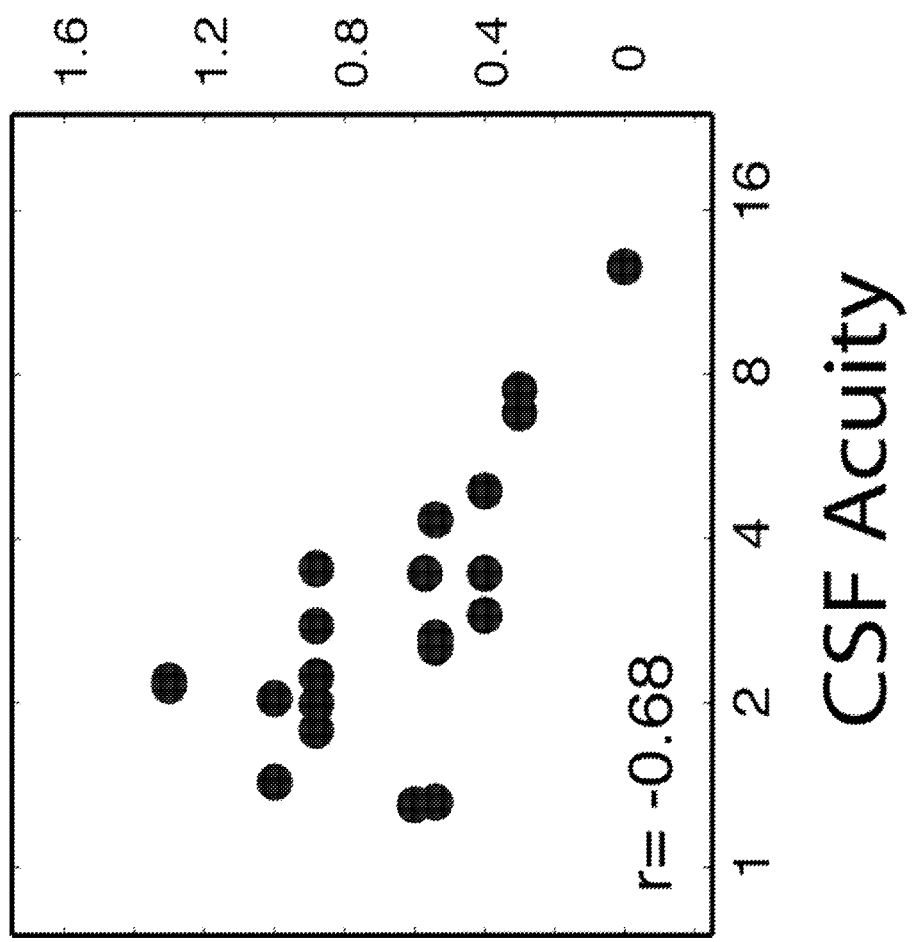
FIG. 11 is a scatter plot showing the relation between logarithm of the minimum angle of resolution (log MAR) acuity measured with a standard Snellen chart and measured CSF acuity.

FIG. 11 is a scatter plot showing the relation between log MAR acuity measured with a standard Snellen chart and measured CSF acuity. To demonstrate that the quick CSF provides contrast sensitivity estimates that are related to more standard clinical vision measures, 21 patients referred to low vision rehabilitation were tested with the quick CSF, the Pelli-Robson contrast sensitivity chart, and standard Snellen acuity test. FIG. 11 demonstrates that high contrast sensitivity acuity measured with the quick CSF is correlated with high Snellen acuity (lower log MAR is higher acuity).

Figure 12:
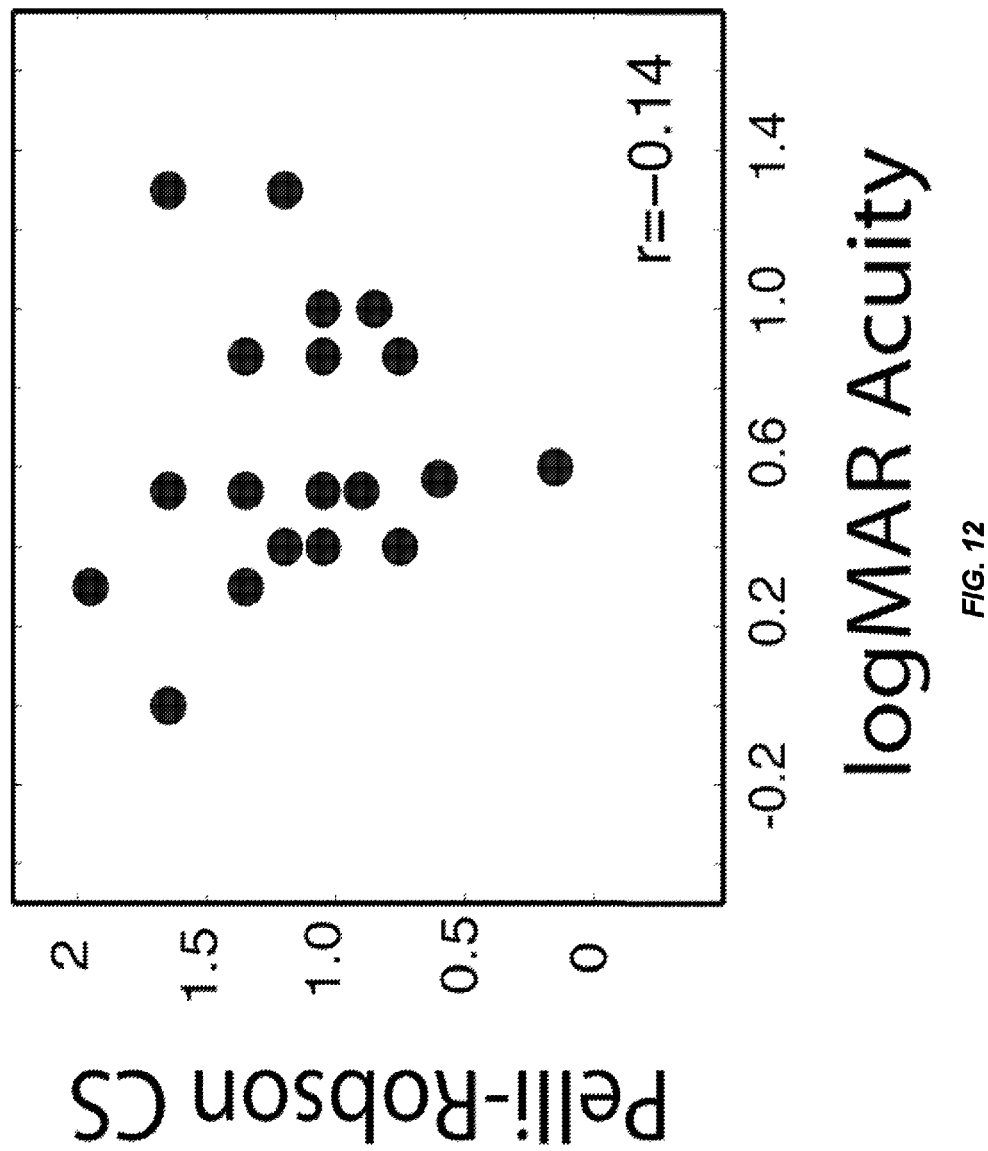
FIG. 12 is a scatter plot illustrating that contrast sensitivity measured with Pelli-Robson chart is not correlated with log MAR acuity in a low-vision population of patients.

FIG. 12 is a scatter plot showing that contrast sensitivity measured with Pelli-Robson chart is not correlated with log MAR acuity in a population of patients referred to low vision rehabilitation. Their visual impairments included age-related macular degeneration and Stargardt's disease.

Figure 13:
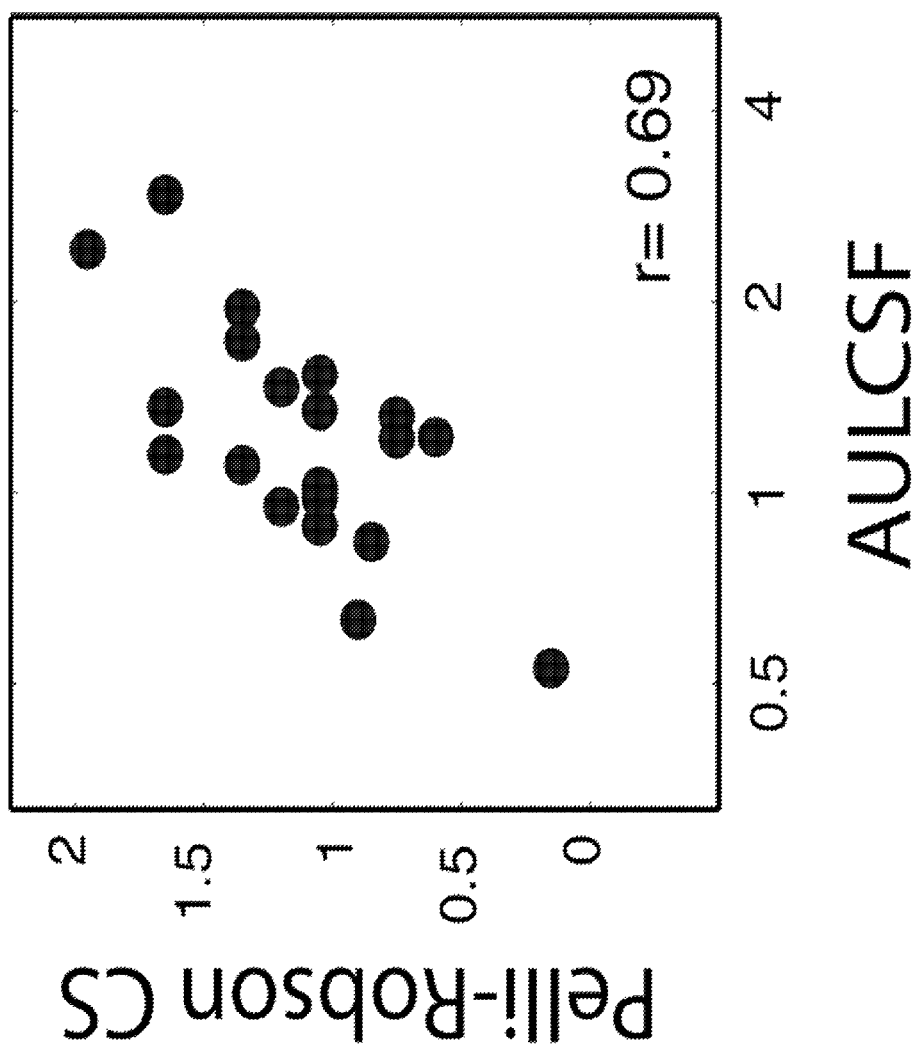
FIG. 13 is a scatter plot illustrating that a contrast sensitivity provided by the AULCSF is correlated with sensitivity estimates provided by a standard Pelli-Robson contrast sensitivity chart.

FIG. 13 is a scatter plot showing that the broad summary of contrast sensitivity provided by the AULCSF is correlated with the sensitivity estimate provided by the standard Pelli-Robson contrast sensitivity chart.

Figures 14A, 14B:
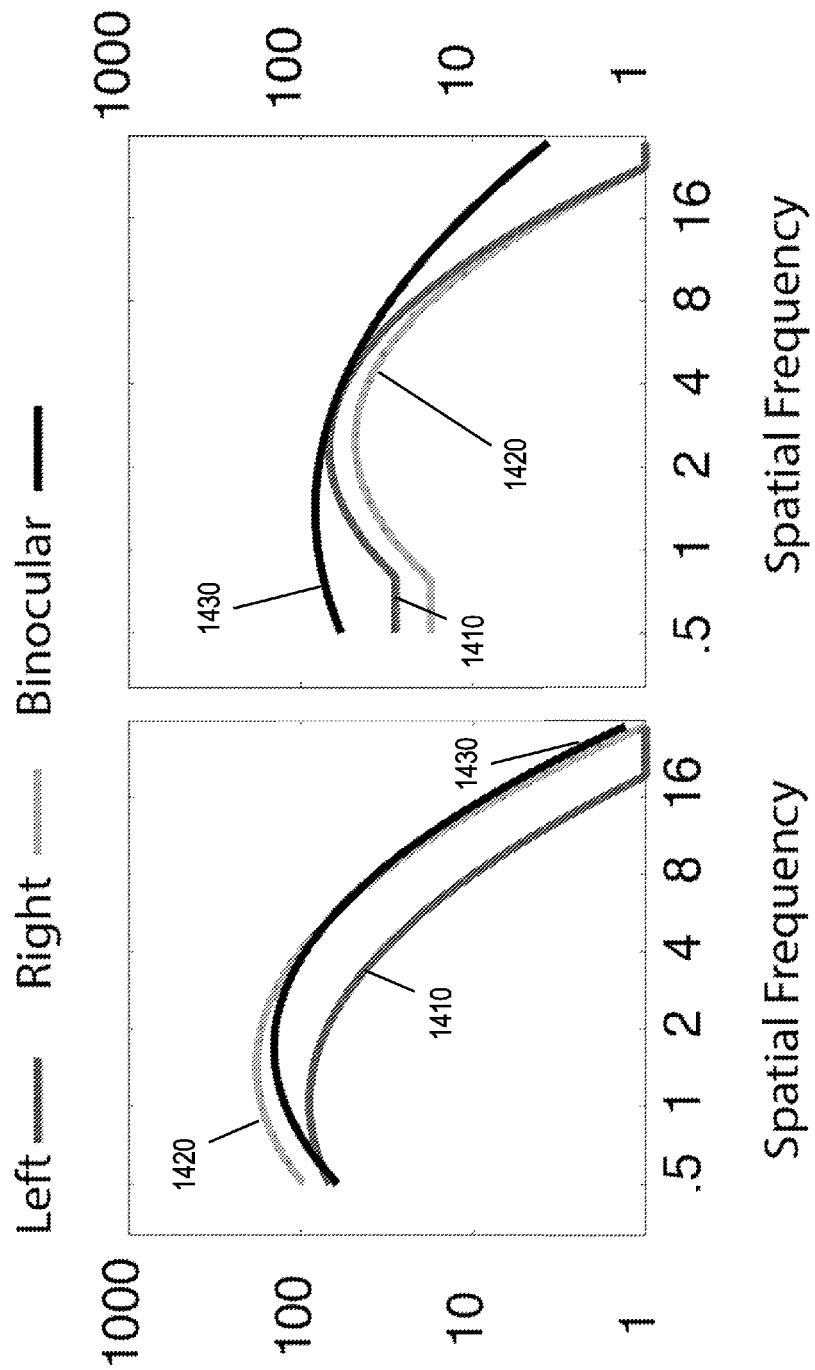
FIG. 14A-B are plots illustrating contrast sensitivity functions obtained from monocular and binocular conditions.

FIGS. 14A and 14B are plots showing contrast sensitivity functions measured in children with amblyopia and normal vision. The quick CSF implemented on a mobile device was used to measure monocular (left 1410; right 1420) and binocular 1430 contrast sensitivity functions. The binocular deficit in amblyopia (FIG. 14A) is evident in the pattern of monocular-binocular functions: the binocular CSF is the same as the CSF of the better eye. In normal vision (FIG. 14B), the binocular function is better than either of the monocular functions.

The following provides an example of an implementation to improve display device contrast resolution. Typical digital display devices can produce only a finite number of different luminance levels or colors. In typical systems, an 8-bit scalar that can take on 256 different values controls the output of each color channel. In order to compensate for the approximately constant relative sensitivity to luminance changes exhibited by the human visual system, typical displays have a nonlinear mapping from input values to physical luminance output. Therefore, the smallest relative luminance increment at mean absolute luminance is typically approximately 1.2 percent for an 8-bit display. The human visual system, however, can distinguish more than 256 different luminance levels. For example, human observers can detect luminance modulations of only 0.5 percent (Kelly, D. H., Motion and vision II Stabilized spatio-temporal threshold surface., J. Opt Soc. Am. 69, 1340-9 (1979); and Kelly, D. H., Motion and vision I Stabilized images of stationary gratings J. Opt. Soc. Ain. 69, 1266-74 (1979)). Therefore, higher bit-depths than 8-bits are required for applications where perceptual fidelity is essential, such as clinical tests of visual function, medical imaging, and professional artwork and photography processing. Specialized hardware capable of 10-bit output is available for these markets but it is complex and expensive.

Dithering has typically been limited to spatial images and trades spatial resolution for an increased luminance resolution. For example, to produce a gray area, half of the pixels are set to black (minimum luminance) and the other half are set to white (maximum luminance). Algorithms that minimize visible artifacts are computationally complex. The bit-stealing algorithm increases luminance resolution by individually controlling the three-color channels. For grayscale patterns, all three-color channels are typically set to the same intensity. Smaller increments than one intensity step on all three channels can be achieved by applying an intensity step on just one or two channels.

The noisy-bit algorithm trades temporal resolution for an increased luminance resolution. The noisy-bit algorithm adds a small amount of uncorrelated luminance noise to each pixel in every screen refresh. Consequently, for fractional input values the output value for this pixel will randomly vary between the nearest integer value below and the nearest integer value above the input value. On average, both over time and over groups of pixels, the output value will approximate the fractional input value. For example, an input value of 127.5 will lead to an output value of 127 in roughly half of all screen refreshes and 128 in the remaining refreshes. Because typical displays run at 60-120 screen refreshes per second and the human visual system is relatively insensitive at high spatiotemporal frequencies, the percept is that of the fractional mean output value. While the noisy-bit algorithm is conceptually simple, it requires sampling of a random number for every pixel in each screen refresh, which is computationally expensive. Embedded devices such as mobile tablets with high-spatial resolution displays may sample several hundred million random numbers every second.

Deterministic temporal patterns can be added to each pixel dependent on the fractional part of its intensity values. For example, for an intensity value of 127.1, a repeating sequence of nine zeros and one 1 is added to the pixel in ten consecutive screen refreshes, so that the average output of this pixel corresponds to 127.1. (This holds for every ten consecutive screen refreshes; in the noisy-bit method, the average output depends on the nondeterministic sequence of random numbers and could be one of 127.0, 127.1, . . . 127.9, 128.0). The increment every n-th frame can become visible if the temporal pattern is the same for large areas with the same fractional intensity. Therefore, a random phase offset assigns to each pixel. For example, a fractional intensity of 127.25 for four neighboring pixels can lead to the addition of 0, 0, 0, 1 to the first pixel; 0, 0, 1, 0 to the second pixel; 0, 1, 0, 0 to the third pixel; and 1, 0, 0, 0 to the fourth pixel. On average, each possible temporal pattern assigns to a quarter of all pixels. The computation of a random phase onset can require only one random number to be sampled per pixel for the whole duration of stimulus presentation, which can be in the hundreds of screen refreshes.

Modern graphics pipelines operate with dedicated graphics processors (GPU) and video memory that are distinct from the central processing unit (CPU) and main memory. Transfers between the two types of memory are relatively expensive. The noisy-bit method for each screen refresh either requires a) generation of random numbers for each pixel on the CPU with a costly subsequent transfer to video memory; or b) generation of random numbers on the GPU, which requires additional memory accesses to record the state of the random number generators for each pixel. With the given approach, only one memory transfer of a random phase onset map is required at the beginning of stimulus presentation. For subsequent screen refreshes, only a single scalar indicating the frame number transfers to the graphics pipeline. From this scalar and a few simple arithmetic operations can compute the correct intensity for each pixel.

The efficient improvement to the grayscale and color resolution of device displays would be useful for embedded devices dedicated to clinical tests of visual function, medical imaging, and professional artwork and photography processing.

The following provides an example implementation related to a wireless mobile device. Features of the current subject matter can be implemented in Objective-C on an Apple iPad 2 device with a 900 MHz ARM A5 CPU and 512 MB of memory. Wherever possible, results of complex computations can be stored in look-up tables to minimize runtime. As a reference, a MATLAB implementation was used running on a desktop computer (Apple iMac) with a 2.7 GHz Intel i5CPU and 4 GB of memory.

Sixteen different spatial frequencies can be evaluated, log-spaced from 0.64 to 20.6 cycles per degree of visual angle. Stimuli were horizontally oriented Gabor patches with a support (+/−3 s.d.) that corresponded to six cycles. Contrast ranged from 0.2% to 100% in 48 log-spaced steps. Therefore, 768 unique stimuli could be displayed.

In a two-alternative forced-choice paradigm, subjects were presented with a task to report whether the briefly presented Gabor target was presented to the left or right of fixation. The contrast sensitivity function represented thresholds defined at the 75% correct performance level. The density of a finite grid of possible parameter combinations was 333944 grid nodes and the number of Monte Carlo samples from the Bayesian prior used for the pre-trial calculation of expected information gain used was 1000 samples.

The iPad display can show 256 unique grayscale tones. OpenGLshaders were used to further increase grayscale resolution (up to 0.2% contrast increments, the smallest increments used in our experiments) by adding spatio-temporal luminance patterns outside the limits of human visual perception.

Three experiments empirically validated the reliability, accuracy, and flexibility of the tablet-based CSF test. For the same observers, contrast sensitivity assessment obtained from tablet-based test was evaluated (Experiment 1), compared with that obtained from laboratory CRT-based tests (Experiment 2), and it was evaluated how the tablet-based test tracked contrast sensitivity changes due to blur conditions (Experiment 3).

In a first experiment, to assess method reliability, contrast sensitivity of four observers (aged 28-36 years; three male, one female; all normal or corrected-to-normal vision) was evaluated by repeated assessment on the tablet. All observers gave informed consent and experiments were carried out in accordance with the Declaration of Helsinki.

Each observer completed four test runs of 120 trials each; during the experiment, observers sat in a darkened room and held the device at 60 cm distance (roughly arm's length). The center of the screen displayed a fixation marker. White markers that indicated the scale (spatial frequency) of the upcoming stimulus and framed the potential locations, i.e. the centers of the left and right screen hemi-field, preceded each trial. The target locations were centered approximately 2.25 degrees from fixation. Stimuli presented in one of these locations for 250 ms, where contrast linearly ramped up and down for the first and last 60 ms, respectively. A subject tapping the tablet screen in one of the hemi-fields registered a response.

A second experiment assessed the accuracy of measures obtained in Experiment 1 using specialized lab equipment. The same four observers completed four tests of 120 trials each. The setup comprised of an iMac workstation computer connected to a carefully calibrated, analog CRT display (LaCie 22-inch electron blue IV running at 1024 by 768 resolution and a refresh rate of 120 Hz), using a video attenuator providing more than 14 bits of grayscale resolution. Despite its analog nature, the CRT has a aperture grill that imposes a finite spatial resolution; for the tablet device, fixed array of pixel-driving transistors limited resolution (1024 by 768 pixels, 60 Hz refresh rate). In order to keep the retinal angle covered by a single pixel constant across both tablet and CRT setups, the test viewing distance for the CRT-based test was doubled to 120 cm. Mean screen luminance was also fixed at 67 cd/m on both setups; luminance calibration was performed with a PR-655 SpectraScan (Photo Research, Inc., Chatsworth, Calif., USA) photometer. In principle, the tablet can show a much wider range of luminance values of up to 400 cd/m. keyboard response registered observers' localization responses for the CRT-based test.

A third experiment evaluated the flexibility and range of the tablet-based test by assessing contrast sensitivity under blur conditions. The same four subjects took the tabled-based test four times while wearing refractive lenses (+4 diopters were added to the subject's regular correction when necessary).

The CSF metrics calculated included the AULCSF, which provides a broad measure of contrast sensitivity across all frequencies, and sensitivity estimates at individual spatial frequencies, (1, 1.5, 3, 6, 12, and 18.5 cycles per degree), which were specified by standards for clinical testing of ophthalmic devices.

Figure 15:
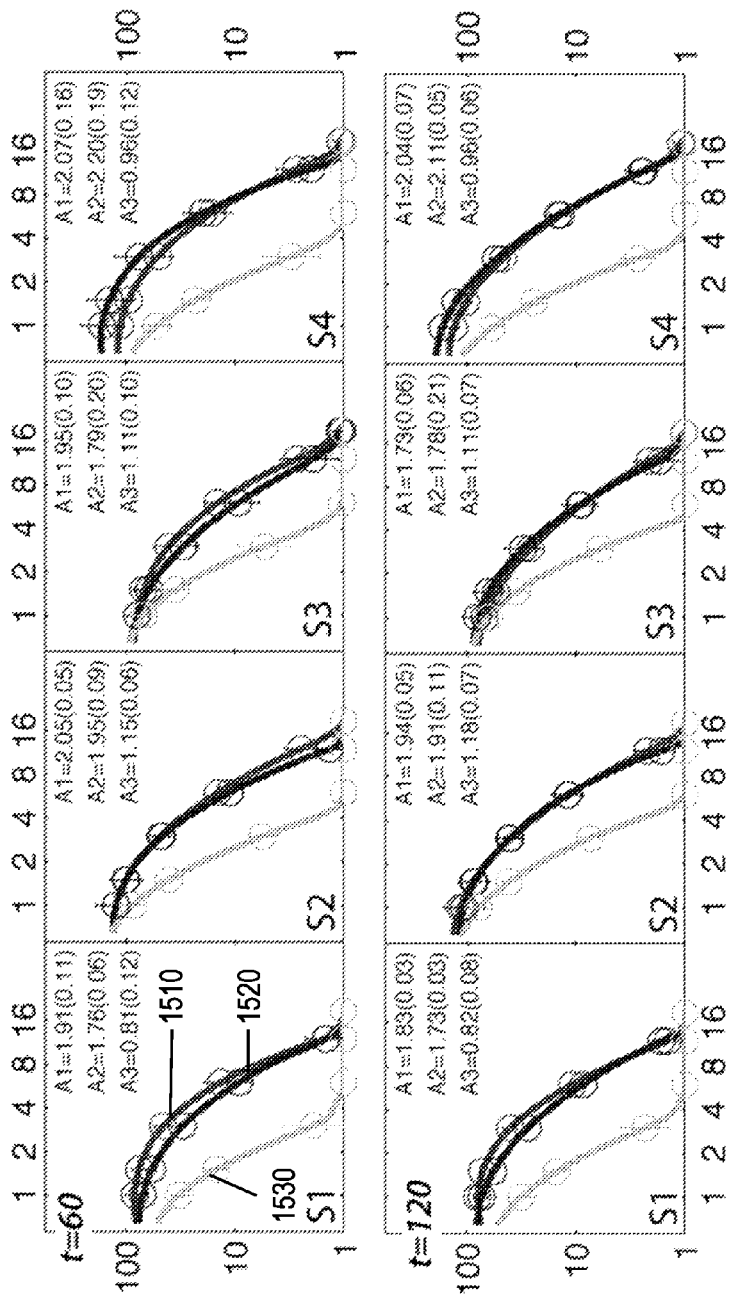
FIG. 15 is a plot presenting contrast sensitivity estimates obtained in three experiments.

FIG. 15 is a plot presenting CSF estimates obtained in the three experiments; each individual panel presents three CSFs (Experiments 1-3) obtained from one subject, with data from each subject presented in different columns, and data from different test-cutoffs (60 or 120 trials) presented in different rows. For the sensitivity estimates at individual spatial frequencies (1, 1.5, 3, 6, 12, and 18.5 cpd), error bars denote the variability (+/−1 standard deviation) of sensitivity estimates across four runs. The mean CSFs and individual sensitivities obtained across four runs are presented for the tablet-based test (Experiment 1; 1510), the CRT-based test (Experiment 2; 1520), and the tablet-based test under blur conditions (Experiment 3; 1530). The A1, A2, and A3 values presented in inset represent the mean and standard deviation of AULCSF estimates obtained in Experiments 1-3. FIG. 15, which presents the tablet-based CSFs (1530), demonstrates that the AULCSF estimates are lower for blur conditions (mean difference=0.986 for 60 trials and 0.868 for 120 trials; 95% limits are +/−0.375 for 60 trials and 0.441 for 120 trials). The reliability of AULCSF estimates were 28.7% and 19.3% for 60 and 120 trials.

The maximal sensitivities were observed at the low frequencies, and were consistently less than 1%. These results are consistent with previous studies of parafoveal visual sensitivity. Reliability was characterized across tablet-based runs by the coefficient of repeatability (COR), which describes the 95% limits expected for repeated measurements. For AULCSF measures, the COR limits were (calculated in percent relative to mean AULCSF): +/−15.4% for 60 trials and +/−8.23% for 120 trials. This high precision value reflects that 95% of retest values fall within 16% of the mean AULCSF estimate.

For estimates of individual sensitivities (see Table 1), the COR values for mid-range spatial frequencies ranged from 0.22 to 0.40 for 60 trials, and 0.18 to 0.37 for 120 trials. The COR value for the highest spatial frequency is especially low 0.134, though this was affected by the sensitivity values of 0, due to peripheral presentation. These values compare favorably to those reported for current contrast sensitivity charts, which range from 0.25 to 0.54 for Vistech, and 0.22 to 0.60 for FACT.

| SF (cpd) | CO | COR | Δ sens | Δ sens |
|---|---|---|---|---|
| 1 | 0.2 | 0.185 | −0.024 | −0.026 |
| 1.5 | 0.2 | 0.184 | −0.001 | −0.013 |
| 3 | 0.3 | 0.179 | 0.038 | 0.004 |
| 6 | 0.3 | 0.143 | 0.095 | 0.012 |
| 12 | 0.3 | 0.373 | 0.139 | 0.047 |
| 18.5 | 0.1 | 0.088 | 0.012 | 0.009 |

Table 1 (above) illustrates coefficient of reliability (COR) for tablet-based test after 60 and 120 trials, and mean difference in sensitivity between tablet and CRT after 60 and 120 trials.

For independent validation of the tablet-based test, Experiment 2 evaluated the quick CSF results obtained on specialized laboratory equipment. The CSFs obtained from the CRT-based test demonstrated excellent agreement with those obtained from the tablet. Agreement between CSF metrics was obtained with tablet and CRT-based tests were characterized. For the AULCSF estimates, the mean difference between methods and their 95% limits of agreement were 3.4% and +/−21.2% for 60 trials, which decreased to 0.01% and +/−13.8% with 120 trials. Mean differences in sensitivity for individual frequencies were <0.05; this difference is much lower than the levels of contrast sensitivity change considered to be clinically meaningful (0.30 log units). It can therefore be concluded that the tablet-based and CRT-based tests provide indistinguishable assessments of contrast sensitivity.

Blur-induced contrast sensitivity deficits were much smaller at low spatial frequencies. This general pattern is the same demonstrated in previous studies. For individual sensitivities at spatial frequencies demonstrating observable sensitivities (1.0, 1.5, and 3.0 cpd), the COR values were 0.313, 0.310, and 0.681 for 60 trials and 0.268, 0.241, and 0.425 for 120 trials. Again, these values for the 95% limits of repeated measurements compare favorably with assumed levels of clinically meaningful contrast sensitivity changes (0.30 log units).

That the rapid and precise contrast sensitivity assessments obtainable with specialized lab equipment can be obtained with a mobile tablet device has been demonstrated. Further, consistent measurements of maximal sensitivity at low-contrast levels that are typically impossible on mobile displays, based on their low bit depth have been demonstrated. For example, the Nike sensory system suffers from these constraints, as it does not present stimuli or measure thresholds lower than 1% on its TFT display. The tablet-based test does not suffer from this ceiling effect, as it reliably measures thresholds below 1% with both CRT-based and tablet-based tests.

Despite limited hardware resources, a tablet-based implementation is fast enough to meet real-time demands. CSF estimates were stable across several test runs and were comparable to those obtained with specialized equipment, a high-end workstation setup with a high-grayscale resolution analog display. Furthermore, the example was sensitive enough to accurately and rapidly describe blur-induced vision loss.

Test precision fundamentally constrains the definition of clinically meaningful changes in vision and the design of clinical studies. In Experiment 1, test precision (COR values correspond to standard deviations of 0.082 to 0.14 log units) were much lower than that historically considered for contrast sensitivity testing (standard deviation is 40 log units). For the design of clinical studies, the estimates of the needed sample sizes rely on power calculations that in turn depend on the expected variability of outcome measures. For example, (as demonstrated in Annex F of ANSI Z80 American National Standard for Ophtalmics: Multifocal Intraocular Lenses; 12-2007), 122 subjects are required to measure a contrast sensitivity change of 0.15 log units, with an outcome measure exhibiting a standard deviation of 0.40 log units (assuming a power of 90% with a 95% significance level). However, because the sample size estimate depends on the square of the test's standard deviation, reducing the standard deviation in half (from 0.40 to 0.20) reduces the sample size estimate by a factor of four, from 122 to 31. Such reduction in clinical trial design can be quite valuable for early stage trials.

Without in any way limiting the scope, interpretation, or application of the claims appearing below, a technical effect of one or more of the example embodiments disclosed herein may include one or more of the following: contrast sensitivity testing efficiency and speed being improved; use of a pre-task to seed an inference algorithm reduces the number of stimuli that are required to be presented to a subject in order to obtain an accurate measurement of contrast sensitivity; an improved assessment of functional vision.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:

1. A method comprising:
    receiving data characterizing a result of a first visual sensitivity test assessing capacity to detect spatial form across one or more different target sizes and different contrasts, the results of the first visual sensitivity test characterizing a line generated on a spatial frequency image that indicates a transition between a visible contrast and an invisible contrast;
    determining, using the received data, one or more first parameters defining a first estimated visual sensitivity for a first range of contrasts and a second range of spatial frequencies;
    determining, using the one or more first parameters and a statistical inference, one or more second parameters defining a second estimated visual sensitivity for a third range of contrasts and a fourth range of spatial frequencies by at least presenting a first visual stimulus, receiving a response, and determining a second visual stimulus based at least on the response and at least a rule; and
    providing the one or more second parameters.

2. The method of claim 1, wherein the results of the first visual sensitivity test further includes:
    an indication of at least one of a presence or an absence of targets of differing spatial frequency.

3. The method of claim 1, wherein the first visual stimulus and second visual stimulus include one or more of: a band-pass frequency stimulus, a band-pass frequency letter, and a localized windowed grating.

4. The method of claim 1, wherein each of the first visual stimulus and second visual stimulus includes a flickering and a band-pass filtered letter, wherein one or more of a temporal frequency of the flickering and a spatial frequency of the band-pass filtered letter varies between the first visual stimulus and the second visual stimulus.

5. The method of claim 1, wherein each of the first visual stimulus and the second visual stimulus comprise dynamic band-pass letter charts.

6. The method of claim 1, wherein the one or more first parameters include one or more of a peak sensitivity, a peak spatial frequency, low-frequency truncation, and a bandwidth.

7. The method of claim 1, wherein the first visual sensitivity test is performed using a mobile device.

8. The method of claim 7, wherein the determining the one or more second parameters further comprises:
    providing instructions to view the first visual stimulus at a viewing distance, the viewing distance determined by using a camera associated with the mobile device to measure a viewing distance; wherein the determination of the one or more second parameters is based on the viewing distance.

9. The method of claim 1, further comprising:
    assessing a visual function by at least using the one or more second parameters to compare visual sensitivity based on at least one or more of the following: at different visual field locations, in different illumination conditions, in photopic and mesopic conditions, and at two or more levels of external illumination noise.

10. The method of claim 1, wherein the determining the one or more second parameters further comprises:
    selecting the first visual stimulus based on at least previously determined parameters, the first visual stimulus being a band-pass frequency stimulus and the previously determined parameters characterizing a probability;
    presenting the first visual stimulus using a display;
    receiving a response relating to the first visual stimulus;
    updating the probability based on at least a Bayes rule and a received response; and
    iterating until a stopping criterion is satisfied.

11. The method of claim 1, wherein the providing comprises one or more of a transmitting, a displaying, a storing, and a computing of the one or more second parameters.

12. The method of claim 1, wherein the determining the one or more second parameters comprises:
    iteratively presenting visual stimulus, receiving a response, and determining second visual stimulus for presenting using the response and at least the rule, the rule based on at least a Bayes rule.

13. The method of claim 1, wherein the one or more first parameters are used as a priori values for a Bayesian inference.

14. The method of claim 1, further comprising displaying the first stimulus by adding a deterministic temporal pattern to each pixel, the deterministic temporal pattern based on a fractional part of an intensity of the pixel.

15. An apparatus, comprising:
    at least one processor; and
    at least one memory including computer program code, the at least one memory and the computer program code configured to, with the at least one processor, cause the apparatus to perform at least the following:
    receive data characterizing a result of a first visual sensitivity test assessing capacity to detect spatial form across one or more different target sizes and different contrasts, the results of the first visual sensitivity test characterizing a line generated on a spatial frequency image that indicates a transition between a visible contrast and an invisible contrast;
    determine, using the received data, one or more first parameters defining a first estimated visual sensitivity for a first range of contrasts and a second range of spatial frequencies;

determine, using the one or more first parameters and a statistical inference, one or more second parameters defining a second estimated visual sensitivity for a third range of contrasts and a fourth range of spatial frequencies by at least presenting a first visual stimulus, receiving a response, and determining a second visual stimulus based at least on the response and at least a rule; and provide the one or more second parameters.

16. The apparatus of claim 15, wherein, wherein the results of the first visual sensitivity test further includes:
an indication of a presence or absence of targets of differing spatial frequency.

17. The apparatus of claim 15, wherein the first visual stimulus and second visual stimulus include one or more of: a band-pass frequency stimulus, a band-pass frequency letter, and a localized windowed grating.

18. The apparatus of claim 15, wherein each of the first visual stimulus and second visual stimulus includes a flickering and a band-pass filtered letter, wherein one or more of a temporal frequency of the flickering and a spatial frequency of the band-pass filtered letter varies between the first visual stimulus and the second visual stimulus.

19. The apparatus of claim 15, wherein each of the first visual stimulus and the second visual stimulus comprise dynamic band-pass letter charts.

20. The apparatus of claim 15, wherein the one or more first parameters include a peak sensitivity, a peak spatial frequency, a low frequency truncation, and a bandwidth.

21. A non-transitory computer readable medium including computer code, which when executed by a computer processor provides operations comprising:
receiving data characterizing a result of a first visual sensitivity test assessing capacity to detect spatial form across one or more different target sizes and different contrasts, the results of the first visual sensitivity test characterizing a line generated on a spatial frequency image that indicates a transition between a visible contrast and an invisible contrast;

determining, using the received data, one or more first parameters defining a first estimated visual sensitivity for a first range of contrasts and a second range of spatial frequencies;

determining, using the one or more first parameters and a statistical inference, one or more second parameters defining a second estimated visual sensitivity for a third range of contrasts and a fourth range of spatial frequencies by at least presenting a first visual stimulus, receiving a response, and determining a second visual stimulus based at least on the response and at least a rule; and providing the one or more second parameters.

22. A method comprising:
receiving data characterizing a result of a first subjective visual sensitivity pre-test assessing capacity to detect spatial form across different contrasts, the first subjective visual sensitivity pre-test including drawing a line on a spatial frequency image that indicates a transition between visible and invisible contrast;

determining, using the received data, one or more first parameters defining a first estimated visual contrast sensitivity function;

determining, using the one or more first parameters as a priori inputs to an iterative Bayesian inference, one or more second parameters defining a second estimated visual contrast function, the iterative Bayesian inference being performed by at least presenting a first visual stimulus, receiving a response, determining a second visual stimulus based at least on the response and at least Bayes rule, and iterating until a stopping condition is satisfied; and providing the one or more second parameters.

23. The method of claim 22 further comprising determining N samples of the a priori inputs using Monte Carlo inverse sampling.

* * * * *

UNITED STATES PATENT AND TRADEMARK OFFICE
CERTIFICATE OF CORRECTION

PATENT NO. : 9,700,201 B2
APPLICATION NO. : 14/399136
DATED : July 11, 2017
INVENTOR(S) : Peter Bex et al.

Page 1 of 1

It is certified that error appears in the above-identified patent and that said Letters Patent is hereby corrected as shown below:

In the Specification

Column 1, Line 12 add Government Support Clause:
--This invention was made with government support under grant numbers EY018664, EY017491, and EY019281 awarded by the National Institutes of Health. The government has certain rights in the invention.--

Signed and Sealed this
Sixth Day of October, 2020

Andrei Iancu
*Director of the United States Patent and Trademark Office*